(12) United States Patent
Lloyd

(10) Patent No.: US 6,428,492 B2
(45) Date of Patent: Aug. 6, 2002

(54) SAFETY SLEEVE TO PROTECT BODY EXTREMITIES

(75) Inventor: Jeffrey S. Lloyd, 1941 Thayer Ave., Los Angeles, CA (US) 90025

(73) Assignee: Jeffrey S. Lloyd, Los Angeles, CA (US)

(*) Notice: Subject to any disclaimer, the term of this patent is extended or adjusted under 35 U.S.C. 154(b) by 0 days.

(21) Appl. No.: 09/338,089

(22) Filed: Jun. 23, 1999

Related U.S. Application Data

(60) Provisional application No. 60/090,615, filed on Jun. 25, 1998.

(51) Int. Cl.[7] ................................................ A61F 5/00
(52) U.S. Cl. .............................. 602/3; 601/151; 601/152
(58) Field of Search ..................... 602/3; 601/151–152; 66/178

(56) References Cited

U.S. PATENT DOCUMENTS

| | | | | |
|---|---|---|---|---|
| 4,502,301 A | * | 3/1985 | Swallow et al. | ............... 66/178 |
| 5,795,312 A | * | 8/1998 | Dye | ........................... 601/151 |

* cited by examiner

Primary Examiner—Jerome W. Donnelly
Assistant Examiner—Lawton Hamilton
(74) Attorney, Agent, or Firm—Sitrick & Sitrick

(57) ABSTRACT

A method to and apparatus to prevent injury and infection of a health-care recipient as a result of anticipated possible complications associated with any ones of a predetermined plurality of health-care procedures. The invention provides specific unambiguous warning indications prohibiting one or more of the aforementioned procedures on the outer surface of a physical barrier which is placed onto said health-care recipient in such a way that the indications are clearly visible. The presence of said barrier is designed to significantly interferes with any reasonable application said plurality of procedures on said recipient.

26 Claims, 19 Drawing Sheets

SAFETY SLEEVE TO PROTECT BODY EXTREMITIES

RELATED APPLICATIONS

This application is a continuation of provisional application Ser. No. 60/090,615 filed Jun. 25, 1998.

FEDERALLY SPONSORED RESEARCH OR DEVELOPMENT

Not Applicable.

BACKGROUND OF THE INVENTION

This invention relates to the field of health care, and specifically to the use of coverings for limbs and other selected body parts to warn and prevent health care providers from inadvertently causing injury or infection to same limbs and selected body parts.

This invention relates to use in hospitals, acute care centers, emergency rooms, doctor's offices, nursing homes, convalescent hospitals, field hospitals, and all other medical, nursing, and health-care facilities.

There are many situations where a body part or extremity must be protected from such a hospital procedure. For example, many women being treated for breast cancer have had the lymph nodes under their arms removed. As a result, because of the risk of developing lymphedema, the arm which no longer has lymph nodes can never be used for intravenous cannula hook-ups, injections, or blood pressure readings.

At the present time, the most commonly used technique for alerting medical personnel to this condition is through the use of a temporary, handwritten note or sign which is typically taped on the wall over a patient's bed. This procedure is fraught with obvious failings: the sign may fall off the wall; it may not be seen; it may be ignored or lost in the clutter; it may be misunderstood or misinterpreted; it may contain incorrect information; and, it may not even be posted at all. Furthermore, a patient may be transported from one room to another, and the warning sign may be left behind.

SUMMARY OF THE INVENTION

It is an object of the present invention to specifically cover and protect a user's limb and/or other body part(s).

It is another object of the present invention to specifically prohibit a health-care provider from providing particular health-care or medical procedures to the user.

It is another object of the present invention to prevent and/or make very difficult particular predefined medical or health-care procedures from being performed on the user's covered and protected body parts.

It is another object of the present invention to prevent injury to the user's body parts protected by the present invention by preventing easy access to same for medical or health-care procedures.

It is another object of the present invention to reduce risk of infection to same protected body parts by preventing easy access to same for medical or health-care procedures.

It is another object of the present invention to force a health-care provider or medical person to explicitly and pro-actively do something in order to circumvent the protection afforded by the present invention in use.

It is another object of the present invention to permit detection of the circumvention of the present invention in use.

These and other aspects and attributes of the present invention will be discussed with reference to the following drawings and accompanying specification.

DETAILED DESCRIPTION OF THE PREFERRED EMBODIMENT

Figure 1:
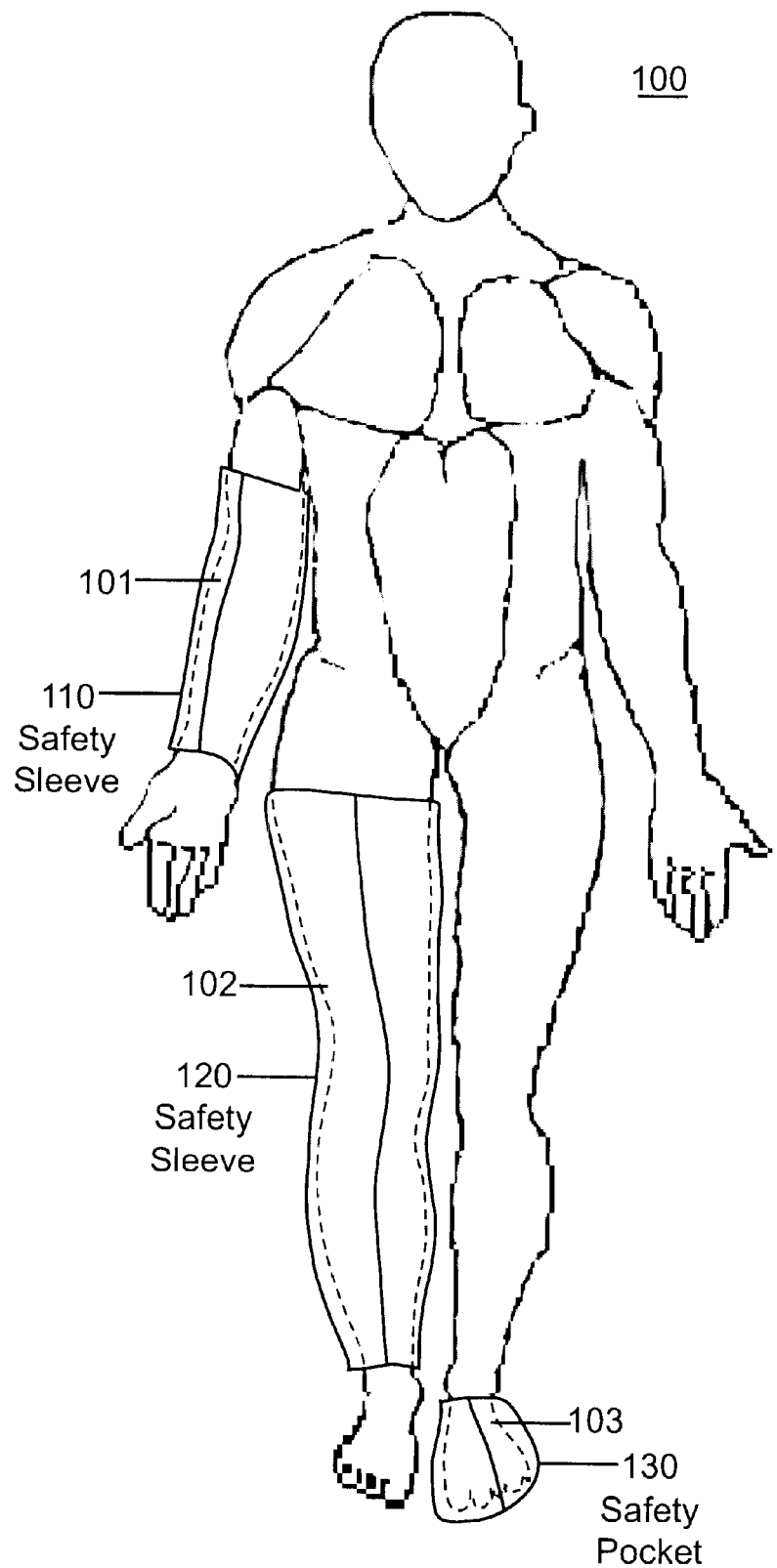
FIG. 1 is an illustration of one embodiment of the present invention as used on a person.

While this invention is susceptible of embodiment in many different forms, there is shown in the drawings, and will be described herein in detail, specific embodiments thereof with the understanding that the present disclosure is to be considered as an exemplification of the principles of the invention and is not intended to limit the invention to the specific disclosed embodiments.

The present invention provides a barrier, both physically and with a warning (visual, audible, etc.) to prevent access to a particular part of a patient, so as to inhibit access to the particular part of the patient to provide a barrier to a medical health care procedure. Various embodiments of the barrier include sleeves (arms, legs, etc.), vests (shoulder, chest, etc.), pockets (hands, feet, ankles, etc.), covers (ears, nose, face), screens, wraps, and others.

In accordance with a first embodiment of the present invention, a sleeve is designed to shield, cover or protect an arm, hand, leg, foot, or any other body part or collection of body parts from a needle injection, intravenous hook-up, blood pressure reading, temperature measurement, or another similar medical procedure. (See FIG. 1, FIGS. 5–10, and FIGS. 17–18.)

The safety sleeve embodiment of the present invention, once applied to the patient as a barrier to a medical health care procedure, eliminates the problems associated with the prior art methods. Through the use of bright colors and descriptive graphics (similar to the familiar "no smoking symbol") emblazoned upon it, the present invention would automatically alert any medical staff member that the covered body part is not to be used for any such medical procedure.

Figure 2:
FIG. 2 is an illustration of a blood pressure warning graphic and text associated with one embodiment of the present invention.
Figure 12:
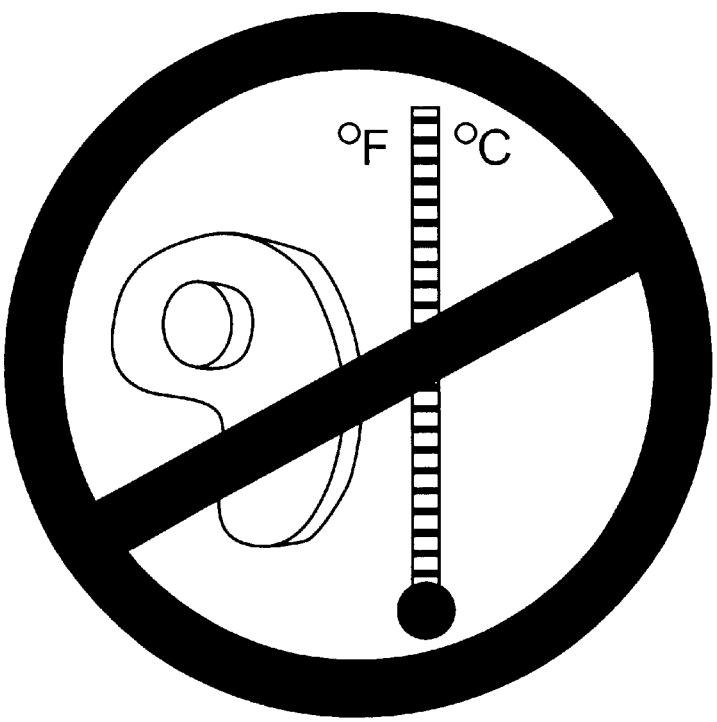
FIG. 12 is an illustration of a temperature warning graphic associated with an embodiment of the present invention.
Figure 13:
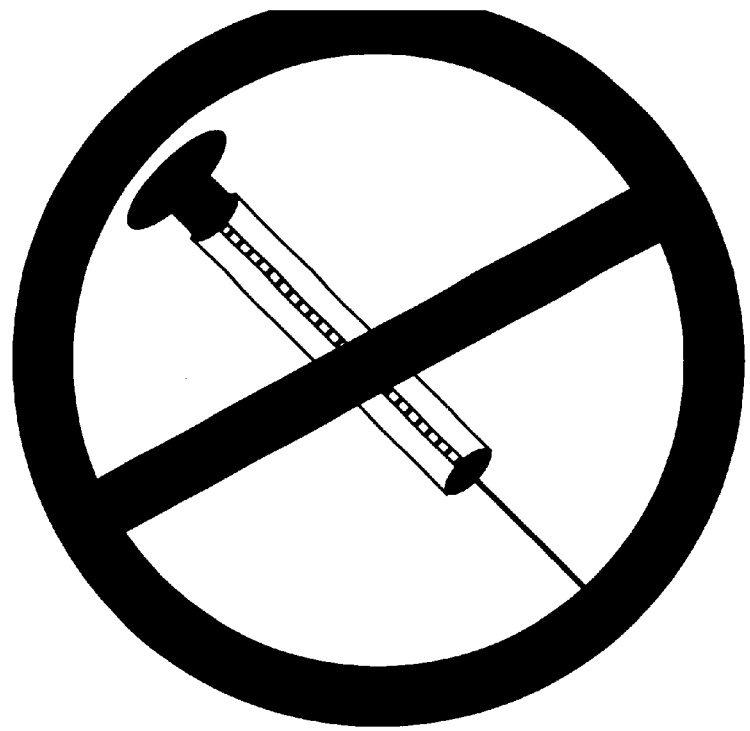
FIG. 13 is an illustration of a hypodermic warning graphic associated with an embodiment of the present invention.
Figure 14:
FIG. 14 is an illustration of a blood pressure warning graphic associated with an embodiment of the present invention.

Some of the more common medical procedures are identified in FIGS. 2–4 and FIGS. 11–16. FIGS. 2 and 14 illustrate alternate embodiments of warning indications for various graphics alerting medical staff that taking a blood pressure reading, and/or using a blood pressure cuff, on the relevant users'body part(s) is prohibited. The graphical warning may be supplemented by a textual description or prohibition. Additionally, the textual warning may be supplied in more than one language.

Figure 3:
FIG. 3 is an illustration of an injection warning graphic and text associated with one embodiment of the present invention.

FIGS. 3 and 13 illustrate alternate embodiments of warning indication graphics alerting medical staff that injecting material, and/or using a hypodermic needle, on the relevant users'body part(s) is prohibited. The graphical warning may be also be supplemented by a textual description or prohibition. As before, the textual warning may be supplied in more than one language.

Figure 4:
FIG. 4 is an illustration of an intravenous warning graphic and text associated with one embodiment of the present invention.
Figure 11:
FIG. 11 is an illustration of a intravenous warning graphic associated with one embodiment of the present invention.

FIGS. 4 and 11 illustrate alternate embodiments of warning indication graphics alerting medical staff that drawing material, or using a cannula, on the relevant users'body part(s) is prohibited. The graphical warning may be also be supplemented by a textual description or prohibition. As before, the textual warning may be supplied in more than one language.

FIG. 12 illustrates an embodiment of a warning indication graphic alerting medical staff that taking or monitoring a temperature of the relevant body part is prohibited.

Figure 15:
FIG. 15 is an illustration of a moisture warning graphic associated with an embodiment of the present invention.

FIG. 15 illustrates an embodiment of a warning indication graphic alerting medical staff that moisture on of the relevant body part is prohibited.

Figure 16:
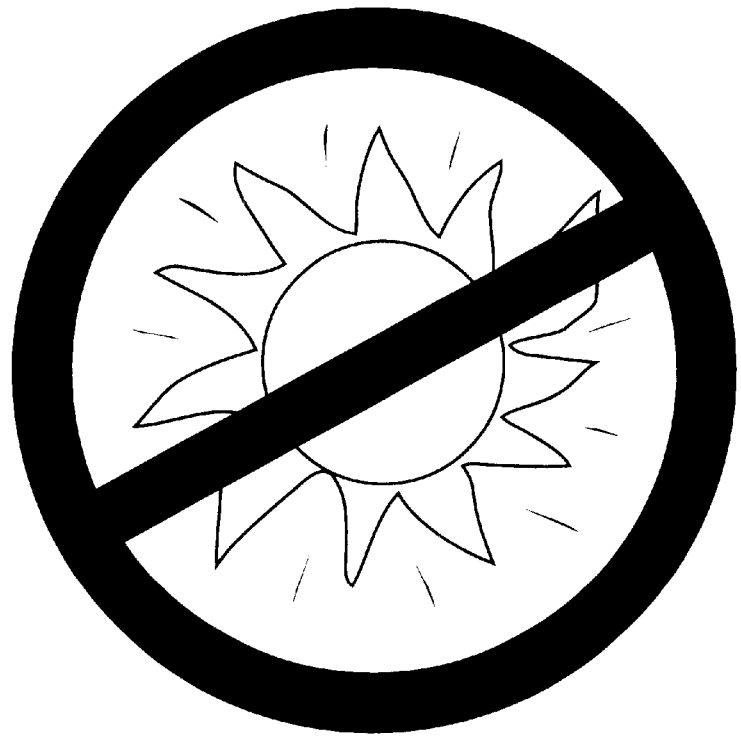
FIG. 16 is an illustration of a bright-light warning graphic associated with an embodiment of the present invention.

FIG. 16 illustrates s an embodiment of a warning indication graphic alerting medical staff that bright light is to be avoided.

The actual graphic images used in accordance with the invention are not limited to the examples shown. Additionally, images (preferably that have been tested to be readily discernable by the medical profession) could supplement or replace the examples shown herein. Any image may be supplemented by textual warnings, and the warnings may appear in any number of languages.

In an alternate embodiment of the invention, the textual warnings stand-alone and are used in lieu of graphic images.

The warning indication graphic images can be one or more of graphics, icons, pictographs, and other visual, audible, or other method or means used to convey information regarding prohibited medical procedures to medical staff.

Figure 26:
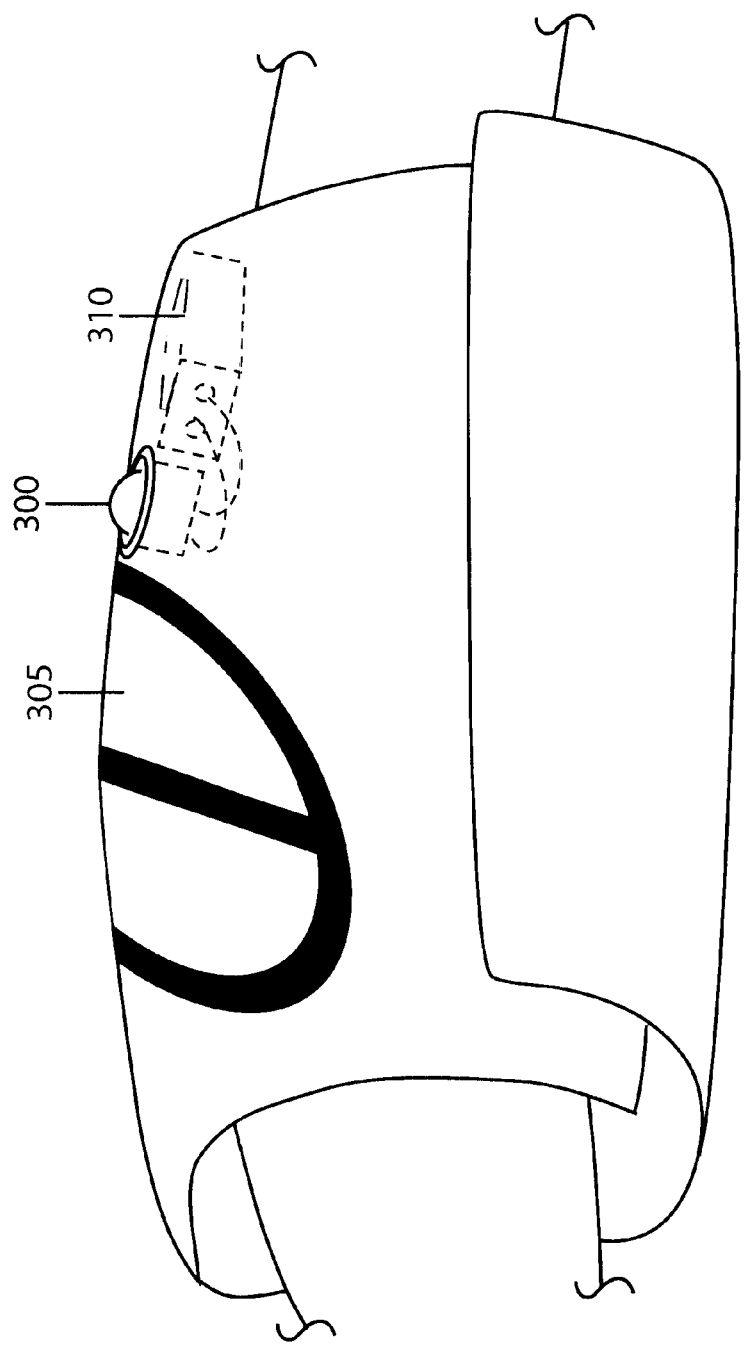
FIG. 26 is an illustration of an alternate embodiment of the present invention including a battery-operated warning light.

In an alternate embodiment as shown in FIG. 26, the invention incorporates an indicator 300 that lights up to draw attention to the warning 305. One of the simplest embodiments is the use of a small battery operated flashing light-emitting diode (LED); such a device could run for weeks on a single battery 310. Other embodiments may include incandescent bulbs, neon or other rare-gas bulbs, and others familiar to one skilled in the arts.

An alternate embodiment features glow-in-the-dark material on the warning, such that the warning would be visible in darkness or near darkness.

In all embodiments, the warning may be affixed to, woven into, painted or printed on, or otherwise made part of or visible from at least one surface of the safety sleeve or other barrier in accordance with the present invention. The key attribute of the warning is that it should provide a specific unambiguous warning indication, to clearly indicate to a health-care provider or medical staff, that specific medical procedures are to be prohibited on the protected body part.

In a preferred embodiment, more than one warning may be visible on the safety sleeve or other barrier embodiment. In this embodiment, each warning is a clear indication of a specific medical procedure that is prohibited for the protected body part. As a result, this embodiment of the invention simultaneously prohibits a plurality of different medical procedures.

In use, multiple instances of the safety sleeve or other barrier embodiment may be used on one patient simultaneously, generally on different body parts. It is also possible to use multiple safety sleeves on one specific body part.

The barrier can be made out of inexpensive, disposable material that is durable enough to remain in place without easily tearing, but flexible enough not to cause any discomfort or pain. Materials suitable for construction of the present invention include paper, cotton, cloth, gauze, silk, plastic, latex, rubber, polyester, Nylon™, Kevlar™, Dacron™, Spandex™, Lycra™, Tyvek™, and other similar materials. The materials can alternatively be chosen for reusability, as durable and washable materials.

In a preferred embodiment, the materials selected for construction would permit easy sterilization of the invention prior to use.

FIG. 1 is an illustration of various embodiments of the present invention as used on a person. Two safety sleeve barriers are shown; one barrier 110 is present on one arm 101 of a person 100, and one barrier 120 is on one leg 102 of a person 100. One safety packet 130 is on one foot 103.

Figure 5:
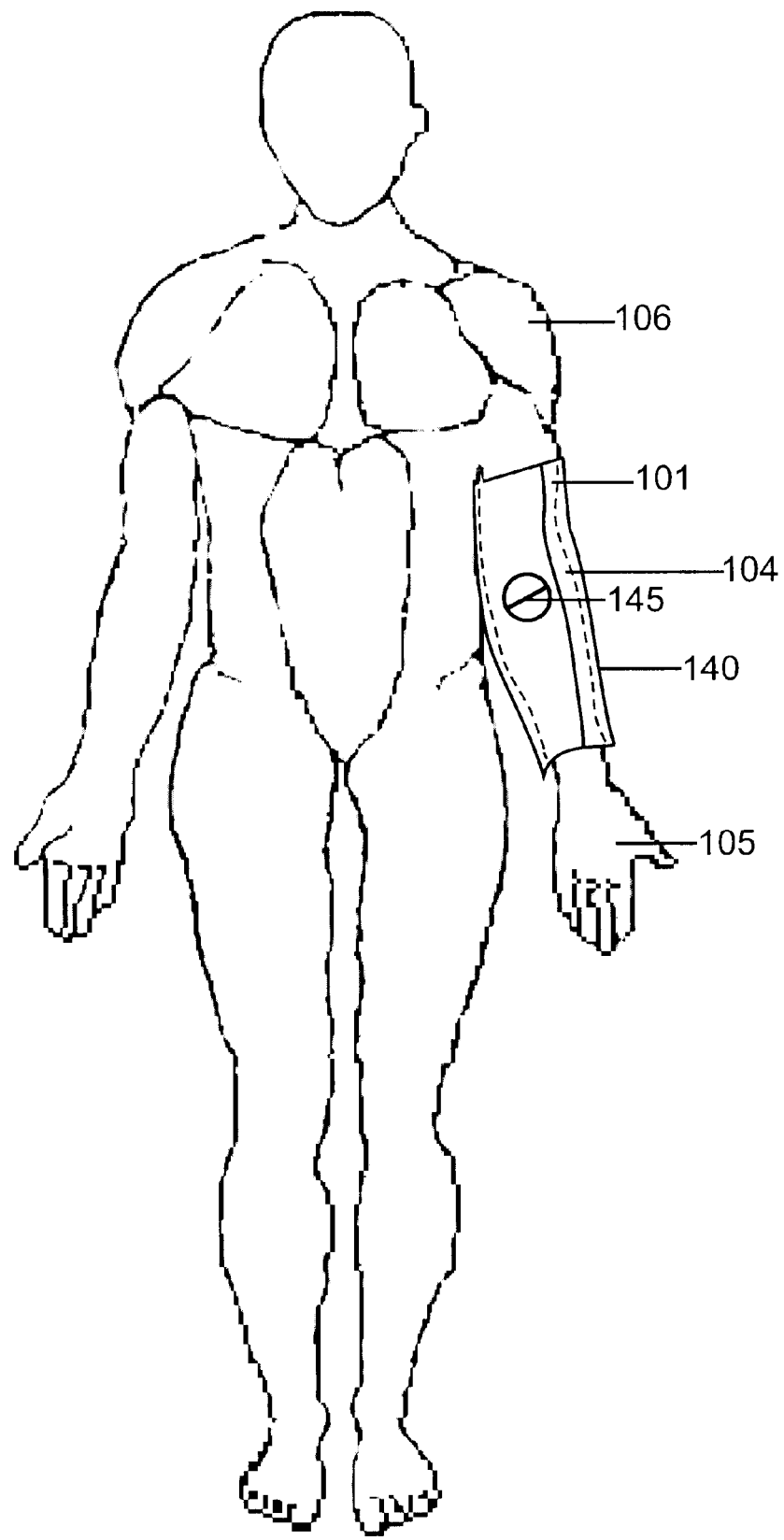
FIG. 5 is an illustration of one embodiment of the present invention as used on a person's arm.

FIG. 5 is an illustration of one embodiment of a barrier sleeve 140 with warning indication 145 as used on a person's arm 101 including an elbow 104 but excluding both the hand 105 and shoulder 106.

Figure 6:
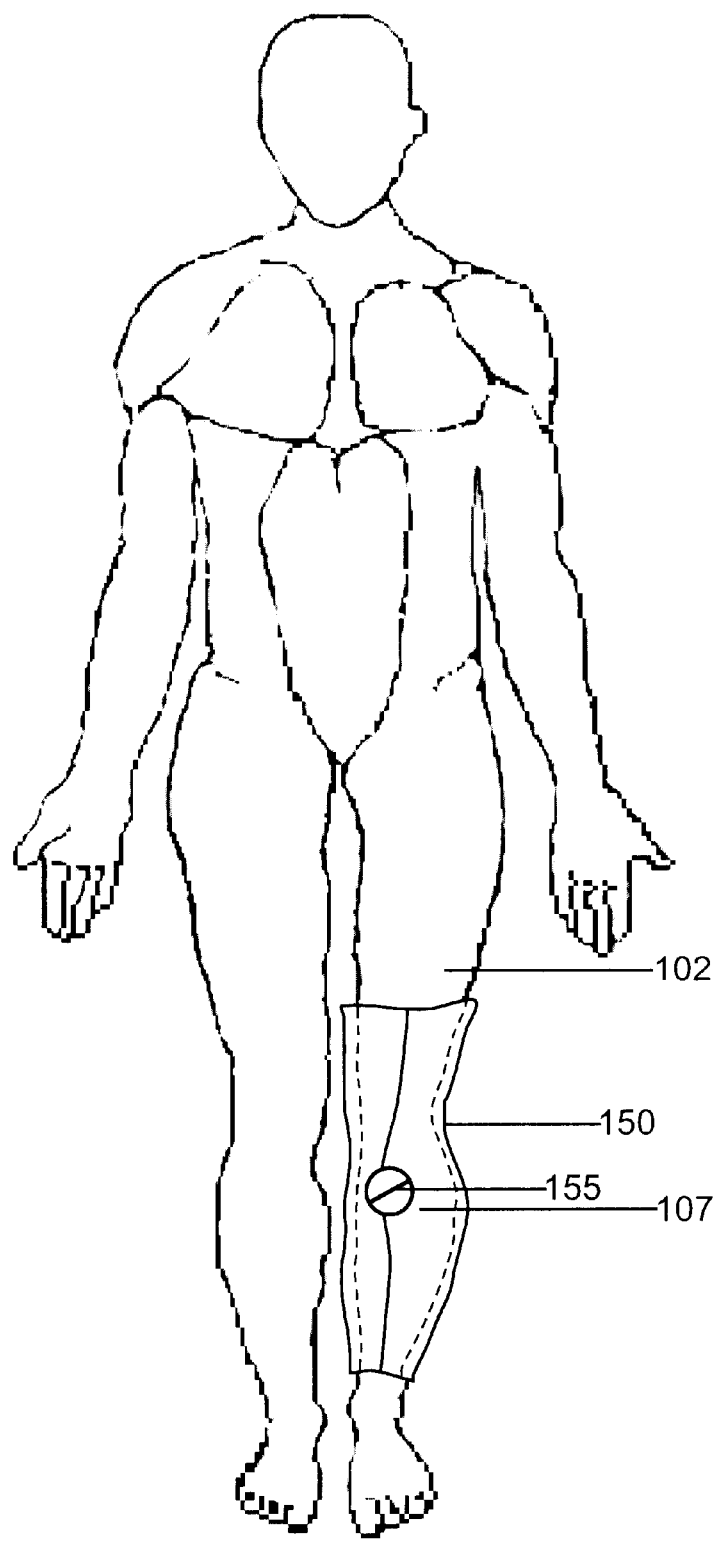
FIG. 6 is an illustration of one embodiment of the present invention as used on a person's leg.

FIG. 6 is an illustration of one embodiment of a barrier sleeve 150 with warning indication 155 on a viewable surface as used on a person's leg 102, including the knee 107 and excluding the pelvis 108 and foot 103.

Figure 7:
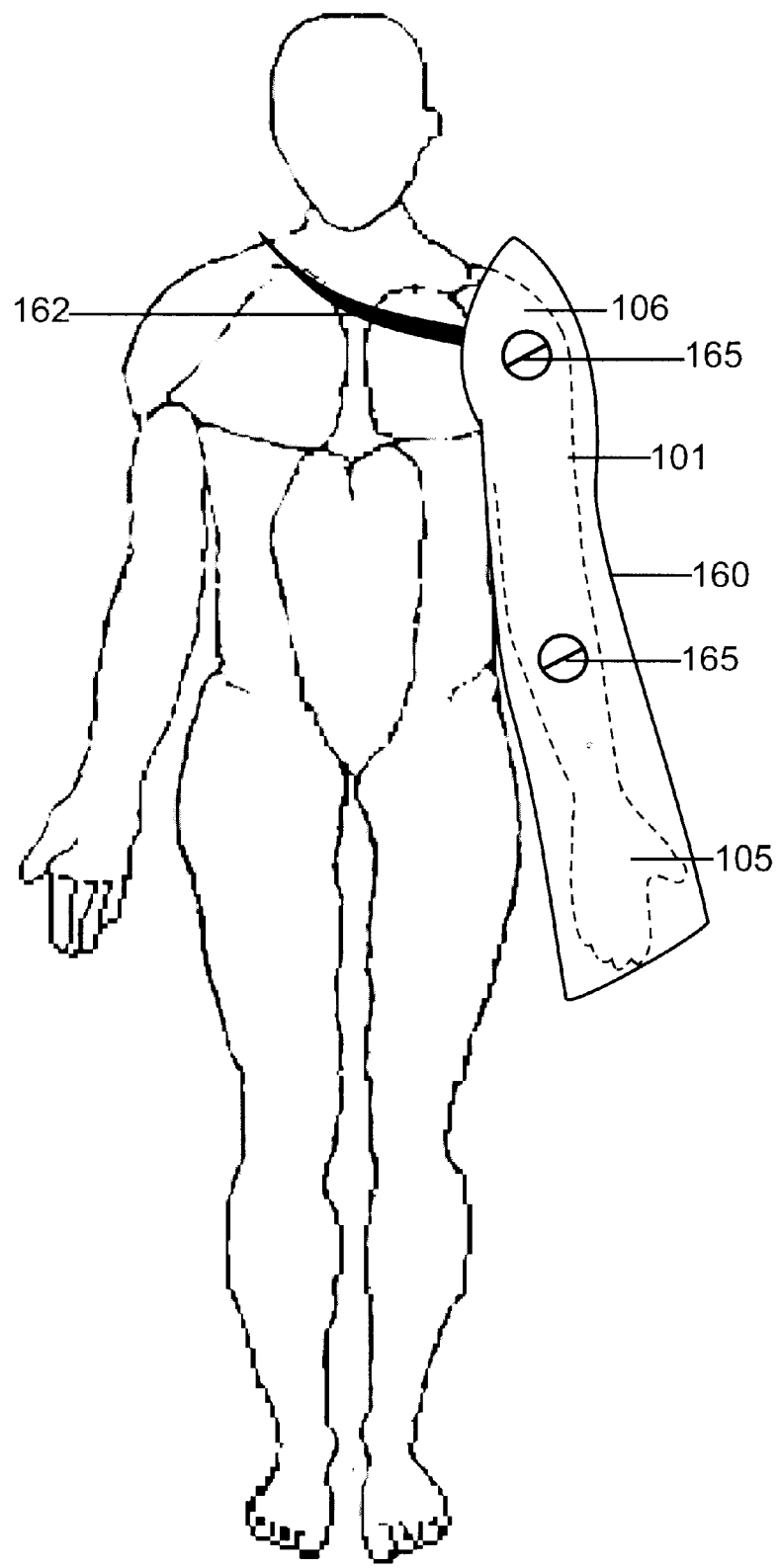
FIG. 7. is an illustration of one embodiment of the present invention as used on a person's arm and shoulder.

FIG. 7 is an illustration of one embodiment of a barrier 160 having a warning indication graphic 165 in accordance with the present invention as used on a person's arm 101 and shoulder 106. This embodiment also illustrates the use of a strap 162 or belt to hold the upper portion of the sleeve in place. The illustrated embodiment has an opening at the bottom end permitting access to the patient's hand 105. In an alternate embodiment, the bottom may be sealed thus preventing access to the patient's hand.

Figure 8:
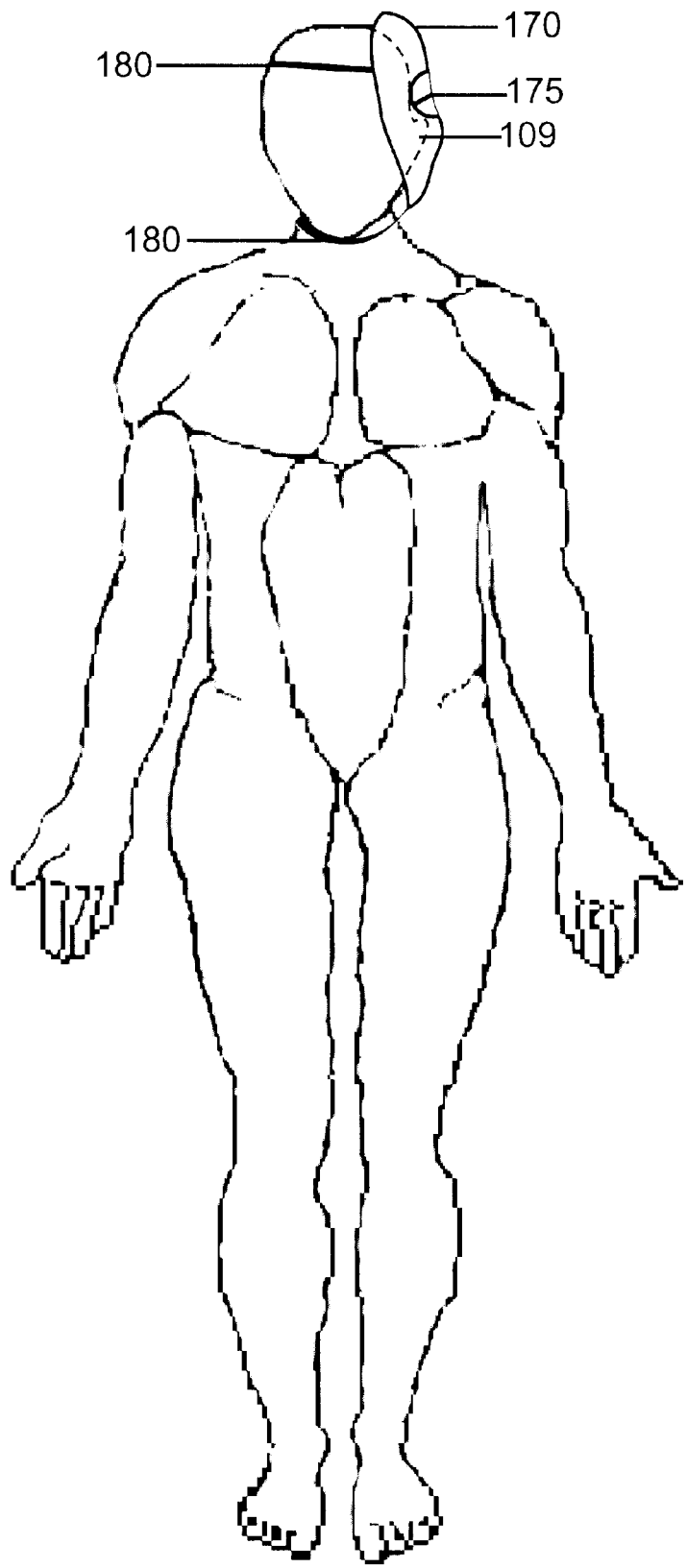
FIG. 8 is an illustration of one embodiment of the present invention as used on a person's ear.

FIG. 8 is an illustration of one embodiment of a barrier 170 having warning indication 175 in accordance with the present invention as used on a person's ear 109. This embodiment also illustrates the use of straps or belts 180 to hold the surface of the protective cover in place. In a preferred embodiment, the straps would be constructed of a stretchable and breathable fabric such as an elastic weave.

Figure 9:
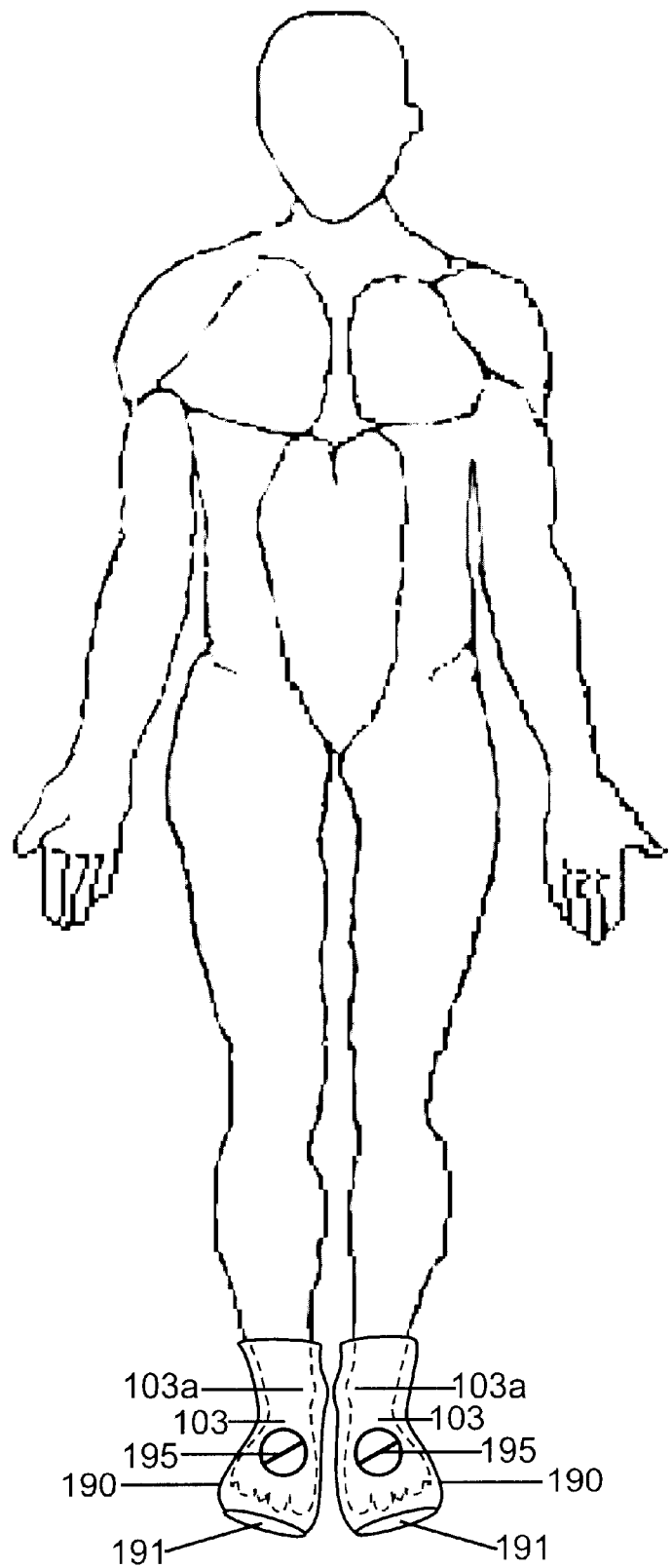
FIG. 9 is an illustration of one embodiment of the present invention as used on a person's feet.

FIG. 9 is an illustration of one embodiment of a barrier 190 having warning indication 195 in accordance with the present invention as used on a person's feet 103. FIG. 9 shows the use of two pockets 190, one on each foot 103, wherein the safety sleeve 190 is closed on the bottom end 191. Each foot 103 is thus protected from the ankle 103*a* on down to the bottom end 191.

Figure 10:
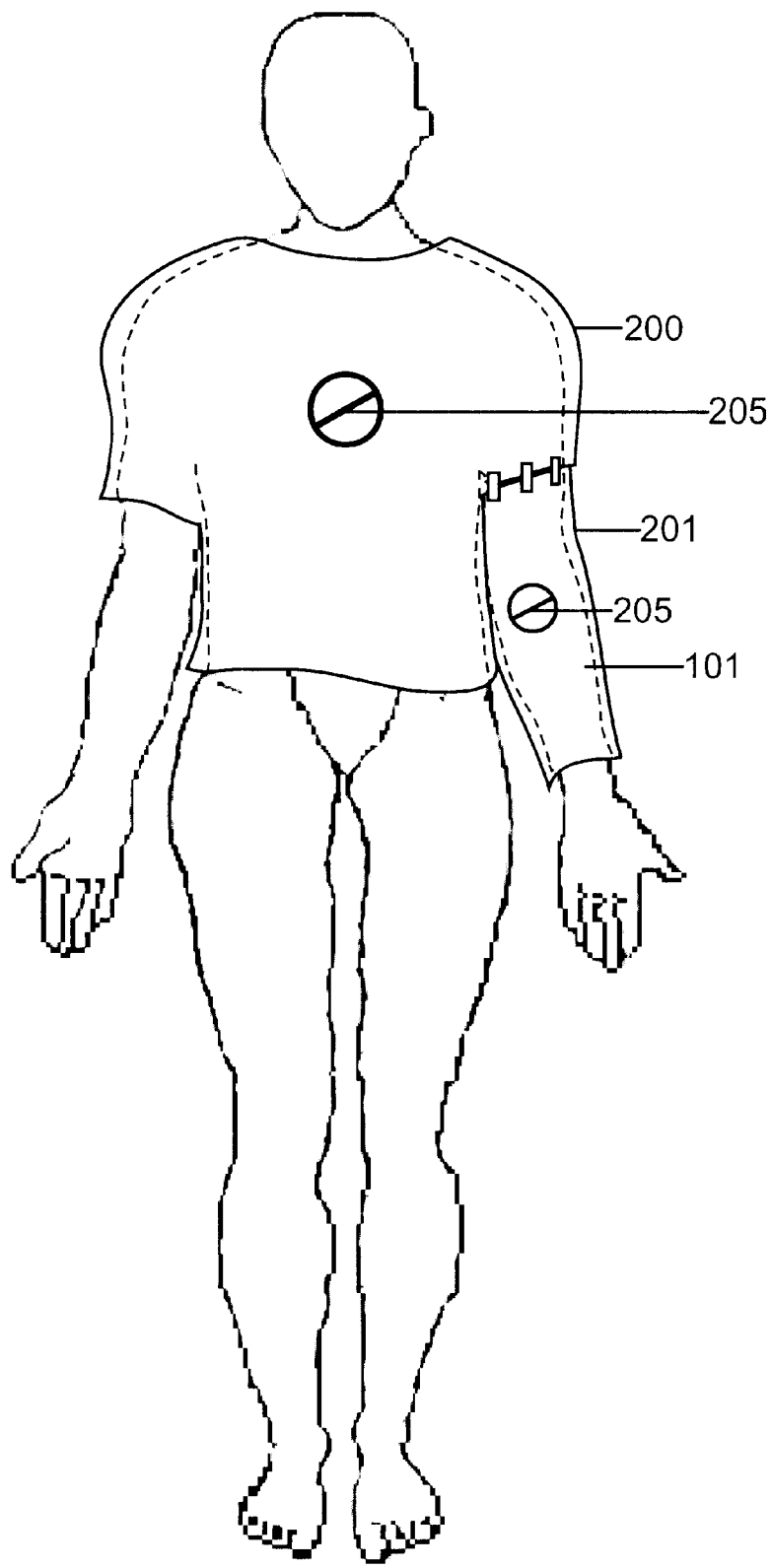
FIG. 10 is an illustration of one embodiment of the present invention as used on a person's arm and upper chest.

FIG. 10 is an illustration of one embodiment of a barrier 200, 201 having warning indication 205 in accordance with the present invention as used on a person's arm 101 and upper chest 111. This illustration shows two safety sleeves 200, 201 of differing design connected via fasteners to form a continuous safety covering.

Figure 17:
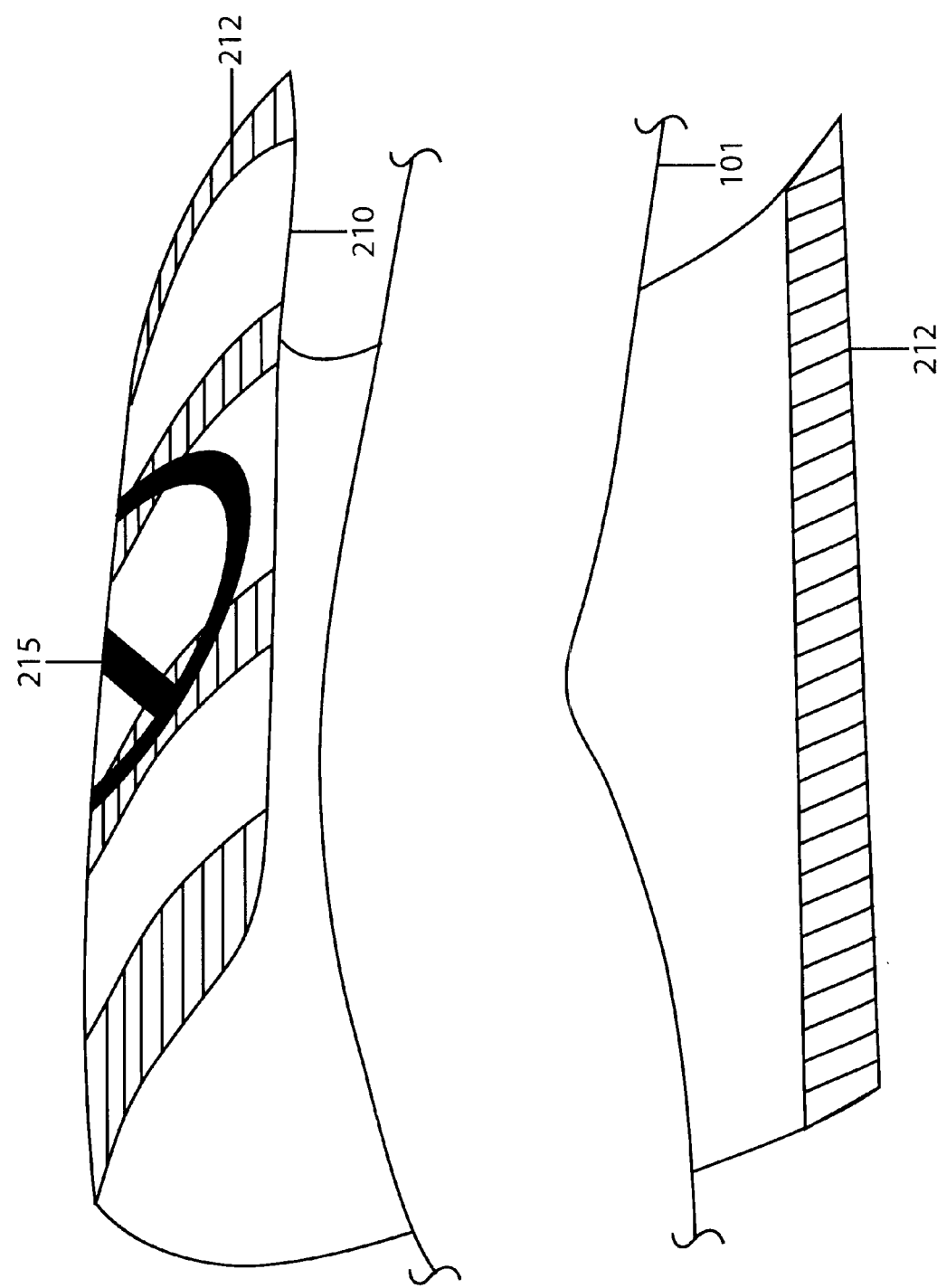
FIG. 17 is an illustration of a one embodiment of the present invention in the process of being applied to a person's arm.

FIG. 17 is an illustration of a one embodiment of a barrier wrap 210 having warning indication 215 in accordance with the present invention in the process of being applied to a person's arm 101. The safety sleeve is shown in the open configuration with fastener means 212 shown, with the arm 101 placed into the center of the sleeve, before the safety sleeve is closed around the patient's arm.

Figure 18:
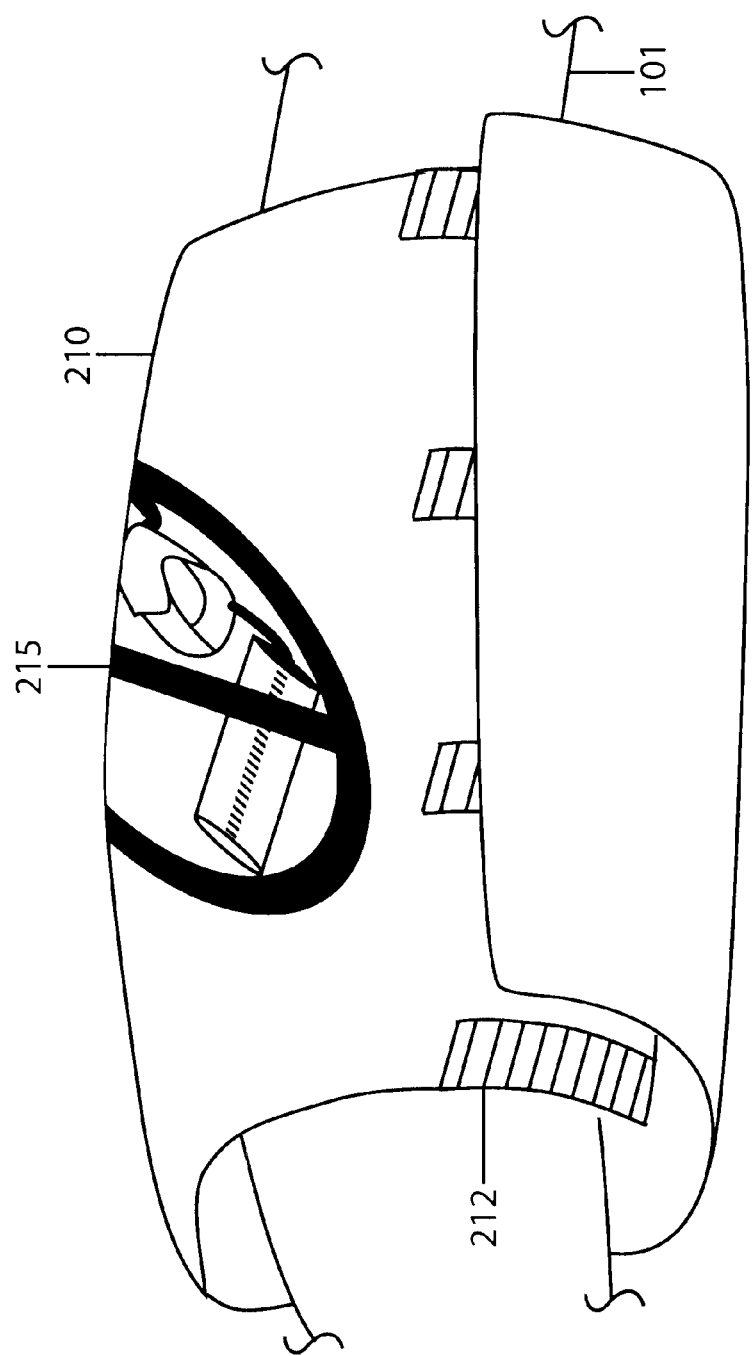
FIG. 18 is an illustration of a one embodiment of the present invention having completed the process of being applied to a person's arm.

FIGS. 18–24 show various embodiments of the present invention including the warning present on the outer surface of the safety sleeve. FIG. 18 illustrates the barrier wrap 210 of FIG. 17, having completed the process of being applied to a person's arm and being in the closed position or configuration. The safety barrier warp sleeve 210 is shown in the closed configuration, with the arm 101 encircled by the safety sleeve.

Figure 19:
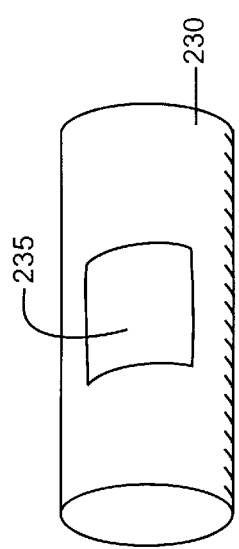
FIG. 19 is an illustration of a one embodiment of the present invention as a single-ended cylindrical pocket.
Figure 20:
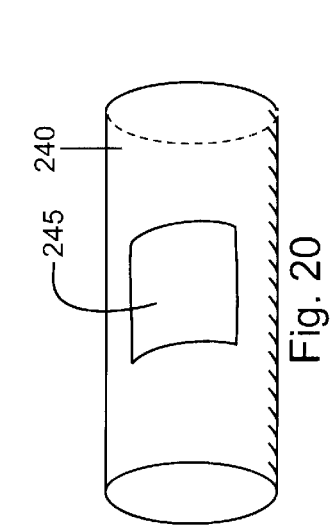
FIG. 20 is an illustration of a one embodiment of the present invention as a double-ended cylindrical sleeve.

Note that FIGS. 17–18 illustrate one seam in the safety sleeve 210. In a preferred embodiment, no seam is present, and the safety sleeve represents a continuous unbroken cylinder as shown in FIGS. 19–20. In another embodiment, the safety sleeve may have a plurality of seams, each with their own respective fastening means.

FIG. 19 is an illustration of one embodiment of a single-ended cylindrical pocket barrier 230 with warning indication 235, suitable for use on a patient's limb or other extremity.

FIG. 20 illustrates one embodiment of a double-ended cylindrical sleeve barrier 240 with warning indication 245, suitable for use on an elbow, wrist, knee, or ankle joint. A larger version of the embodiment shown in FIG. 20 is suitable for use on a torso.

Figure 21:
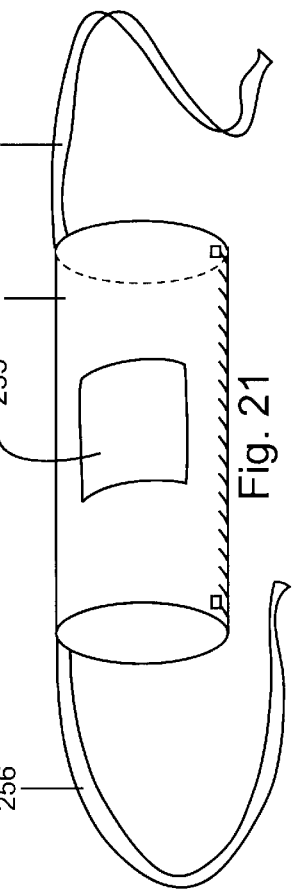
FIG. 21 is an illustration of another embodiment of the present invention as a double-ended cylindrical sleeve including tie straps.

FIG. 21 is an illustration of another embodiment of a double-ended cylindrical sleeve barrier 250 having warning indication 255 including tie straps 256 to assist the positioning and placement of the safety sleeve 250.

Figure 22:
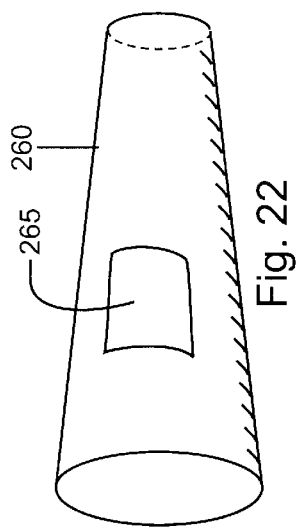
FIG. 22 is an illustration of a one embodiment of the present invention as a double-ended conical sleeve.

FIG. 22 is an illustration of a one embodiment of a double-ended conical sleeve barrier 260 with warning indication 265. This shape is more suitable for some patients to protect lower extremities such as a complete leg.

Figure 23:
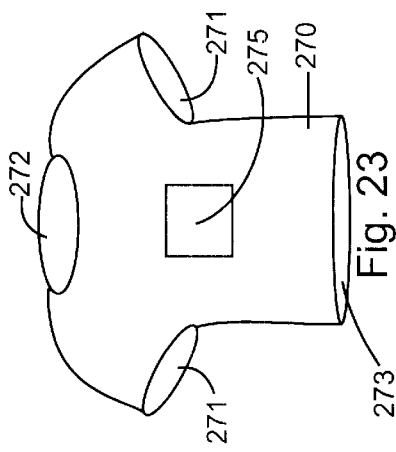
FIG. 23 is an illustration of an alternate embodiment of the present invention as a shirt.

FIG. 23 is an illustration of an embodiment of a shirt barrier 270 having warning indication, comprising holes for arms 271, neck 272, and torso 273.

Figure 24:
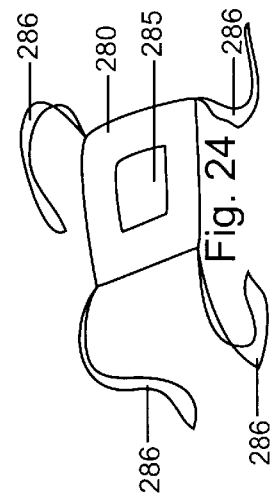
FIG. 24 is an illustration of another alternate embodiment of the present invention as a warning patch with tie straps.

FIG. 24 is an illustration of an alternate embodiment of a warning patch barrier 280 with warning indication 285 with tie straps 286. This embodiment is suitable for very small areas that need protection that would be otherwise difficult to encompass by the other embodiments.

Figure 25:
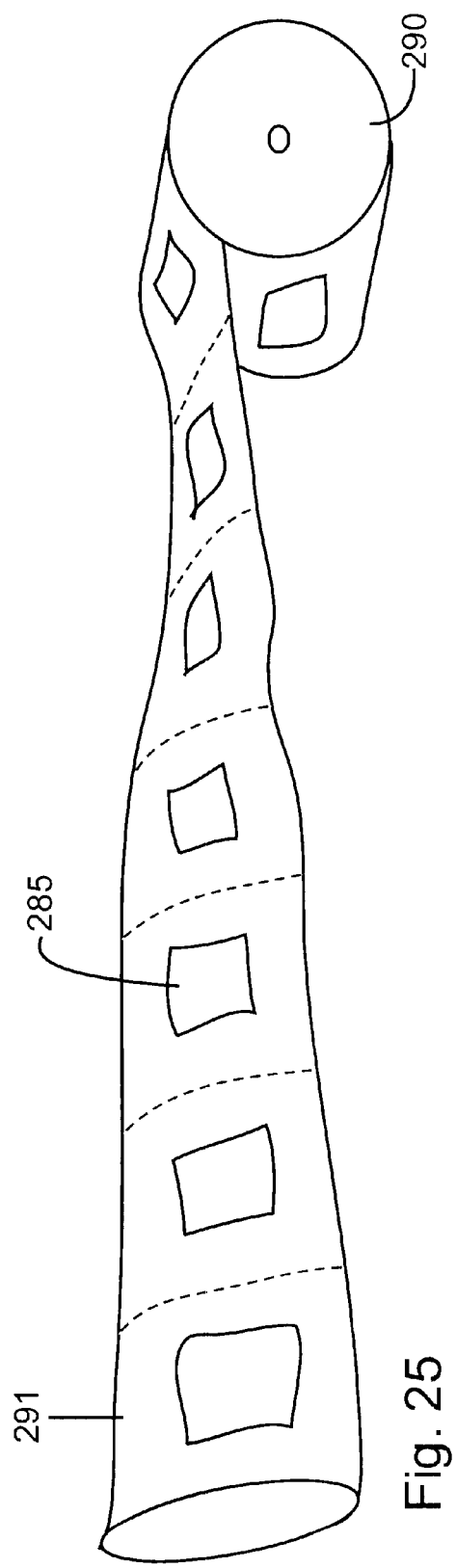
FIG. 25 is an illustration of one embodiment of the present invention supplied as a continuous roll.

FIG. 25 is an illustration of one embodiment of the present invention wherein the barrier is initially supplied as a continuous roll 290. A number of segments 291 of safety sleeve are constructed with perforations separating each segment from the next, and the segments are rolled for distribution. In use, the user would select the number of segments required and tear off that length from the roll, thus reducing waste.

The sleeve would remain in position on a patient through the use of any of the following devices, including self-adhesive strips, hook and loop fasteners, buttons, zippers, hooks and eyes, ties, buckles, belts, pins, string, elastic bands, rubber bands, snaps, clasps, Velcro™ tape fasteners, or any other clasping, fastening, or adhesive device.

The fasteners may be used to fasten solely to other portions of the safety sleeve. In a preferred embodiment, the fasteners may alternatively fasten to elements of the patient's existing clothing, thus permitting additional ease of installation and use of the invention. In an alternate embodiment, the invention may be fastened directly to the patient's skin, using suitable adhesives well-known to those in the medical profession.

In a preferred embodiment, the invention includes a means to detect if the invention has been removed and/or opened at any time during its use. This detection means may utilize any of fragile tape, single-use stickers, color-change chemicals, phase-change chemicals, a mechanical indicator, limit switches, or a position sensor. If the invention has been opened or removed at any time, the detection means provides obvious and unchangeable evidence of such tampering. In one preferred embodiment, the detection means provides an alarm trigger output, which can be used to alert medical or nursing staff at a monitoring station or within some signalling range that the invention has been tampered with.

In addition to tampering and removal, one embodiment of the present invention permits detection of unusual attributes such as elevated or depressed temperature, high or low pH values, presence or absence of moisture, and so on. Additionally, in another embodiment motion inside the safety sleeve can be detected. A different embodiment of the invention permits sensing of blood oxygenation level. Each of these attributes may be used to trigger an alarm or as a data input to an external medical system.

In an advanced embodiment, the safety sleeve includes motion and/or proximity sensors, using any conventional sensing means known to those skilled in the arts, including active and passive infrared (IR), ultrasonic, trembler, and vibration sensors. These sensors may trigger an alarm within some signalling range indicating attempted access or tampering with the safety sleeve by someone external to the patient.

In a preferred embodiment, the material of the safety sleeve is flexible, lightweight, inexpensive, sterile, and disposable. In one embodiment, the safety sleeve may be one of water-resistant, water-proof, or water-tight. In another embodiment, the safety sleeve may be gas-tight permitting air pressurization or vacuum.

Figure 27:
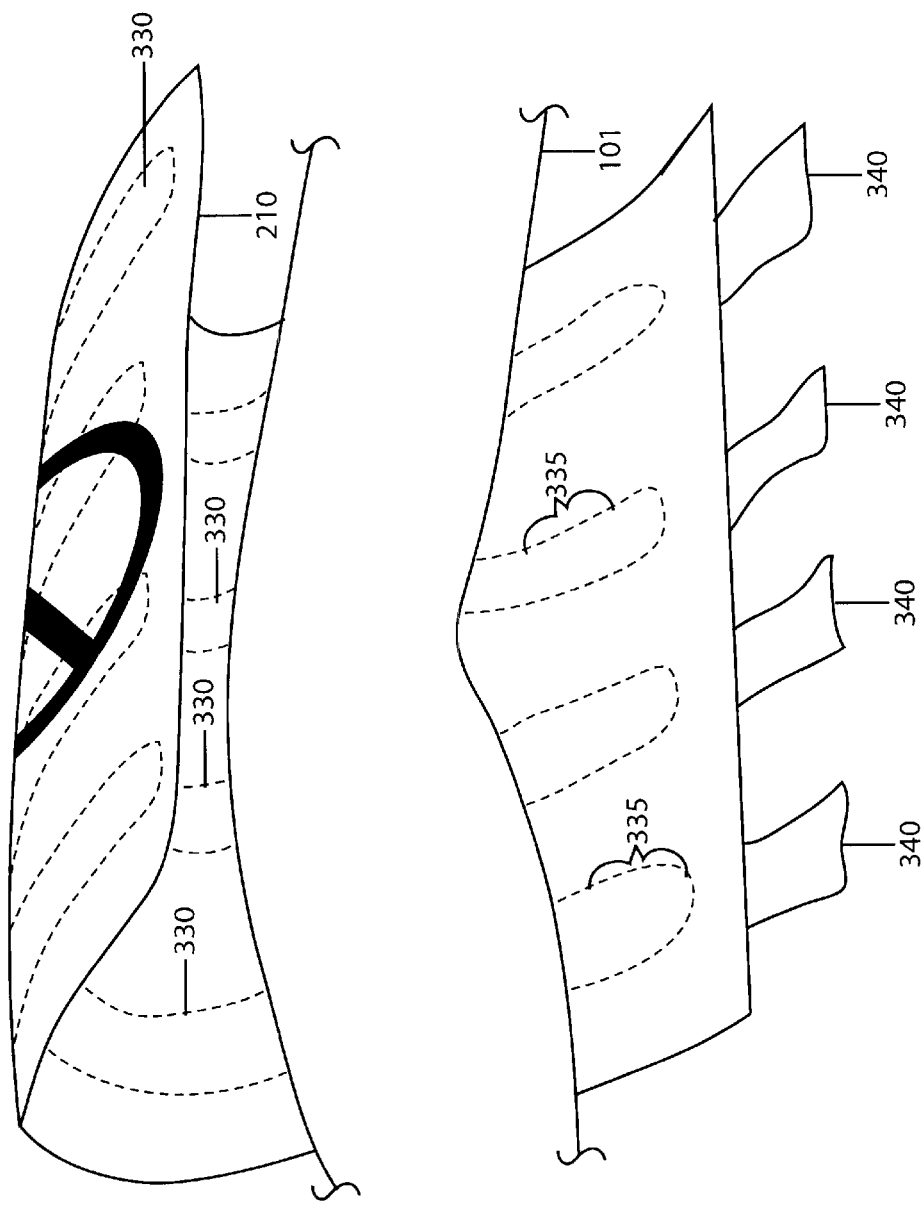
FIG. 27 is an illustration of another embodiment of the present invention which incorporates a support structure and an alternate fastening means.

In one embodiment, as shown in FIG. 27, the safety sleeve incorporates internal support structures to permit the sleeve to maintain a shape or profile independently of the patient's body part These supports may include ribs, rings, stays, splints, restraints, air cushions, water cushions, aerogels, braces, and/or supports. As shown in FIG. 27, support ribs 330 may be affixed to the safely sleeve barrier wrap 210 by means of stitches 335 or other attachment means. Alternatively, the support ribs may be formed as an integral part of the safety sleeve barrier wrap 210. In the illustrated embodiment, self-adhesive tabs 340 are shown to fasten the safety sleeve in place.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed is:

1. An apparatus to provide a barrier with warning to interfere with medical physical access required to give physical treatment to a body portion of a health-care recipient, said apparatus comprising:
    a physical barrier, having an outer surface, placed to block access to said body portion; and
    a warning indication visible on the outer surface for communicating the prohibition to the medical physical access subsequent to the physical barrier being placed to block access to said body portion,
        wherein said warning indication comprises at least an illumination source, and
        wherein said illumination source is at least one of an incandescent light bulb, a rare-gas light bulb, a glow-in-the-dark material, a chemical cold-light, and an light-emitting diode.

2. An apparatus to provide a barrier with warning to interfere with medical physical access required to give physical treatment to a body portion of a health-care recipient, said apparatus comprising:
    a physical barrier, having an outer surface, placed to block access to said body portion; and
    a warning indication visible on the outer surface for communicating the prohibition to the medical physical access subsequent to the physical barrier being placed to block access to said body portion,
        wherein the sensor is one of a proximity sensor, a movement sensor, a temperature sensor, a pH sensor, a moisture sensor, a pressure sensor and an oxygenation sensor.

3. An apparatus to provide a barrier with warning to interfere with medical physical access required to give physical treatment to a body portion of a health-care recipient, said apparatus comprising:
    a physical barrier, having an outer surface, placed to block access to said body portion; and
    a warning indication visible on the outer surface for communicating the prohibition to the medical physical access subsequent to the physical barrier being placed to block access to said body portion,
    wherein said barrier comprises a closeable enclosure, having an open position and a closed position,
    wherein in the open position access is provided to perform said procedure, and
    wherein in the closed position access is inhibited to perform said procedure, and wherein a fastener portion retains said barrier in said closed position.

4. The apparatus as in claim 3, wherein the presence of said barrier significantly interferes with and prevents any reasonable application of said procedure on said recipient.

5. The apparatus as in claim 3, wherein said barrier comprises a sleeve having openings on each end, said sleeve encircling said body portion.

6. The apparatus as in claim 3, wherein said barrier comprises a pocket having a single opening enclosing at least a portion of the body of said recipient.

7. The apparatus as in claim 6 wherein said barrier further comprises a plurality of pockets enclosing a respective plurality of body parts of said recipient.

8. The apparatus as in claim 3, wherein said barrier comprises a covering wrapped around at least one body part of said recipient.

9. The apparatus as in claim 8, wherein said barrier is additionally comprised of attachment means to attach said barrier to clothing of said recipient, wherein the attachment means is at least one of self-adhesive strips, hook and loop fasteners, buttons, zippers, hooks and eyes, ties, buckles, belts, pins, elastic bands, rubber bands, snaps, clasps, and tape fasteners.

10. The apparatus as in claim 3, wherein said barrier is further comprised of a barrier web portion and a barrier fastener portion.

11. The apparatus as in claim 10, wherein said barrier web portion is comprised of at least one of paper, cotton, cloth, gauze, silk, rubber, plastic, epoxy resin, polyolelfins, thermoplastic, polymers, and polyethelyne.

12. The apparatus as in claim 11, wherein said barrier web portion additionally comprises support structure comprising at least one of ribs, rings, stays, splints, restraints, air cushions, water cushions, aerogels, braces, and supports.

13. The apparatus as in claim 10, wherein said barrier fastener portion is comprised of at least one of self-adhesive strips, hook and loop fasteners, buttons, zippers, hooks and eyes, ties, buckles, belts, pins, string, elastic bands, rubber bands, snaps, clasps, and tape fasteners.

14. The apparatus as in claim 3, wherein said warning indication additionally comprises at least one of a graphic image, a color warning, an icon warning, a textual warning, an audible warning, and an illumination source.

15. The apparatus as in claim 5 wherein said barrier further comprises a plurality of sleeves encircling a respective plurality of body parts of said recipient.

16. The apparatus as in claim 14, wherein said warning indication comprises at least said textual warning, and wherein said textual warning is presented in a plurality of languages.

17. The apparatus as in claim 3, wherein said barrier is at least one of water-resistant, water-proof, and gas-tight.

18. The apparatus as in claim 3 wherein said barrier further comprises detection means providing means to detect if the fastener portion has been opened from said closed position.

19. The apparatus as in claim 18 further comprising a detection alarm for providing an indication of the opening of the barrier, responsive to the detection means.

20. The apparatus as in claims 18 wherein the detection means is further comprised of at least one of fragile tape, single-use stickers, color-change chemicals, phase-change chemicals, a mechanical indicator, limit switches, a position sensor, and an alarm trigger.

21. A disposable medical warning safety apparatus for use in blocking prohibited physical treatment access to a body part of a patient's body, the apparatus comprising:

a flexible and lightweight material comprising an outer exterior surface and having a closure thereupon for securing the material around a selected body part to form a barrier to block the physical treatment of the body part, for placement in a loose fit over the body part;

wherein said outer exterior surface provides a warning, subsequent to the placement, alerting of the prohibited physical access relating to the body part for communicating a prohibition to the physical treatment of the body part;

wherein said material forms a barrier to block an injection to the body part, and wherein said warning communicates a prohibition against injection.

22. A disposable medical warning safety apparatus for use in blocking prohibited physical treatment access to a body part of a patient's body, the apparatus comprising:

a flexible and lightweight material comprising an outer exterior surface and having a closure thereupon for securing the material around a selected body part to form a barrier to block the physical treatment of the body part, for placement in a loose fit over the body part;

wherein said material forms a barrier to block application of pressure to the body part, and wherein said warning communicates a prohibition against application of pressure.

23. A medical warning safety shield for placement over a body part of a person to form a barrier and to alert and physically preclude prohibited physical treatment to the body part by another person subsequent to the placement of the shield to form the barrier, the shield comprising:

a lightweight material having an outer surface;

closure means for providing a loose fitting and non-binding closing and holding the material to form a shield to physically preclude the physical treatment to the body part; and warning means to alert said another person against physical treatment to the body part, wherein the warning means is comprised of an audible warning activated responsive to any attempt to provide the prohibited physical treatment.

24. An apparatus to provide a barrier with warning to interfere with medical physical access required to give physical treatment to a body portion of a health-care recipient, said apparatus comprising:

a physical barrier, having an outer surface, placed to block access to said body portion; and a warning indication visible on the outer surface for communicating the prohibition to the medical physical access subsequent to the physical barrier being placed to block access to said body portion, further comprising a sensor associated with the barrier, wherein said warning indication additionally comprises an alarm output, which is triggered responsive to the sensor.

25. The apparatus as in claim 24, wherein the alarm is audible.

26. The apparatus as in claim 24, wherein the alarm output is one of at least one of a light source, an audible output, and a printout.

* * * * *